United States Patent [19]

Fenet

[11] Patent Number: 5,257,976
[45] Date of Patent: Nov. 2, 1993

[54] SINGLE USE DISPOSABLE SYRINGE

[76] Inventor: Emeric G. Fenet, Le Bois Joly, 5 Avenue A., Houchart 13100 Le Tholonet, France

[21] Appl. No.: 690,995
[22] PCT Filed: Jan. 5, 1990
[86] PCT No.: PCT/FR90/00007
§ 371 Date: Jun. 18, 1991
§ 102(e) Date: Jun. 18, 1991
[87] PCT Pub. No.: WO90/07949
PCT Pub. Date: Jul. 26, 1990

[30] Foreign Application Priority Data

Jan. 10, 1989 [FR] France .................. 89 00345

[51] Int. Cl.$^5$ .............................................. A61M 5/00
[52] U.S. Cl. ............................ 604/110; 604/228; 604/218; 128/919
[58] Field of Search ............... 604/110, 187, 218, 220, 604/219, 222, 228; 128/919

[56] References Cited

U.S. PATENT DOCUMENTS

| | | |
|---|---|---|
| 3,934,586 | 1/1976 | Easton et al. . |
| 3,951,146 | 4/1976 | Chiquiar-Arias . |
| 4,731,068 | 3/1988 | Hesse . |
| 4,961,728 | 10/1990 | Kosinski .................. 604/110 |
| 4,979,943 | 12/1990 | Trenner .................. 604/110 |
| 5,037,393 | 8/1991 | Ellgass .................. 604/110 |
| 5,084,017 | 1/1992 | Maffetone .................. 604/110 |
| 5,085,640 | 2/1992 | Gibbs .................. 604/110 |
| 5,149,323 | 9/1992 | Colonna .................. 604/110 |

FOREIGN PATENT DOCUMENTS

| | | |
|---|---|---|
| 0229017 | 7/1987 | European Pat. Off. . |
| 1965761 | 7/1970 | Fed. Rep. of Germany . |
| 8810127 | 12/1988 | World Int. Prop. O. . |
| 8902287 | 3/1989 | World Int. Prop. O. .......... 604/110 |
| 8906146 | 7/1989 | World Int. Prop. O. . |
| 9101768 | 2/1991 | World Int. Prop. O. .......... 604/110 |
| 9112039 | 8/1991 | World Int. Prop. O. .......... 604/110 |

Primary Examiner—John D. Yasko
Assistant Examiner—Mark O. Polutta
Attorney, Agent, or Firm—Ladas & Parry

[57] ABSTRACT

A single use disposable syringe having a piston axially slidable in a barrel for undergoing a retraction movement to fill the barrel with fluid and a forward movement to discharge the fluid from the barrel. An operating rod projects from the barrel for operating the piston and the rod is operatively connected to the piston with capability of relative axial movement therebetween to approach the piston during its forward movement. A flexible finger has one end connected to the piston or rod and a cutting element is provided on the flexible finger in spaced relation from the connected end thereof and facing the barrel. During retraction movement of the piston, the cutting element is retracted from the barrel whereas during forward travel of the piston and approach of the operating rod towards the piston, a deviation member displaces the flexible finger outwardly to produce cutting of the barrel by the cutting element to render the barrel subsequently unusable.

16 Claims, 5 Drawing Sheets

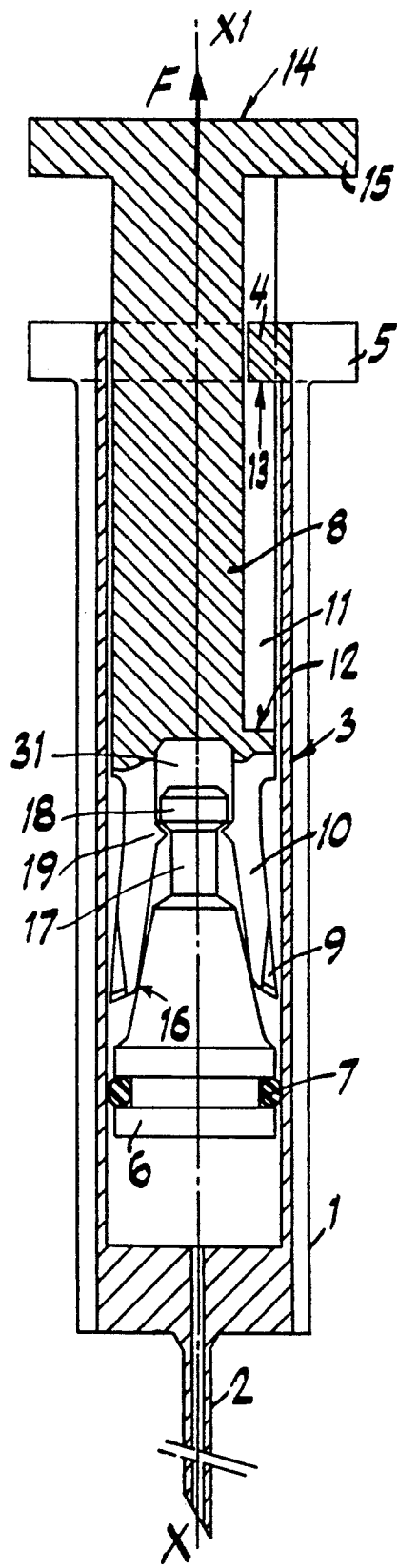
FIG. 1
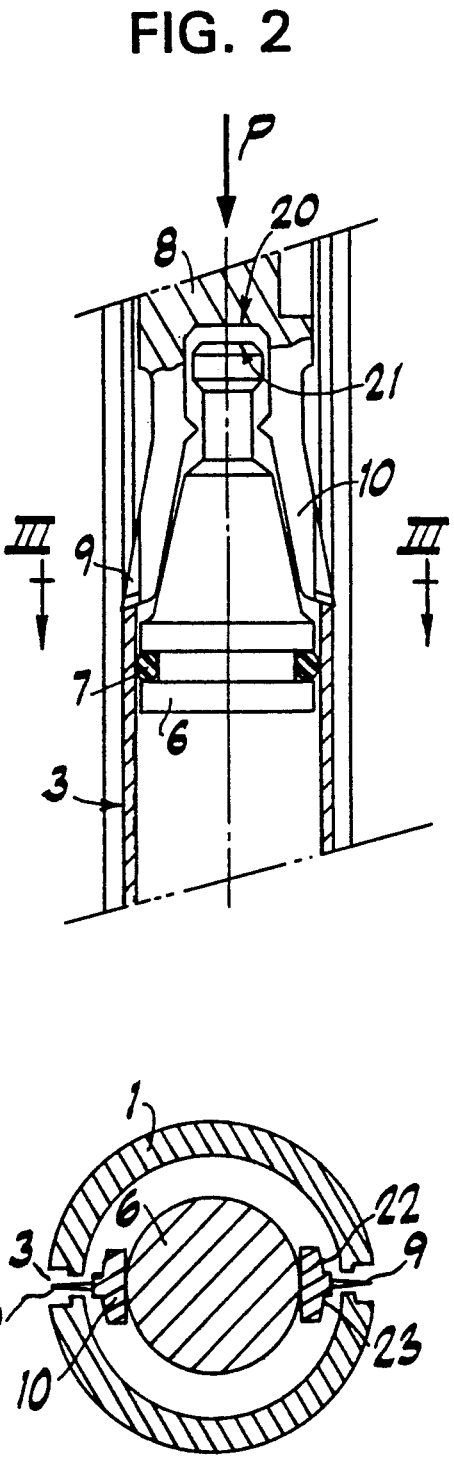
FIG. 2
FIG. 3

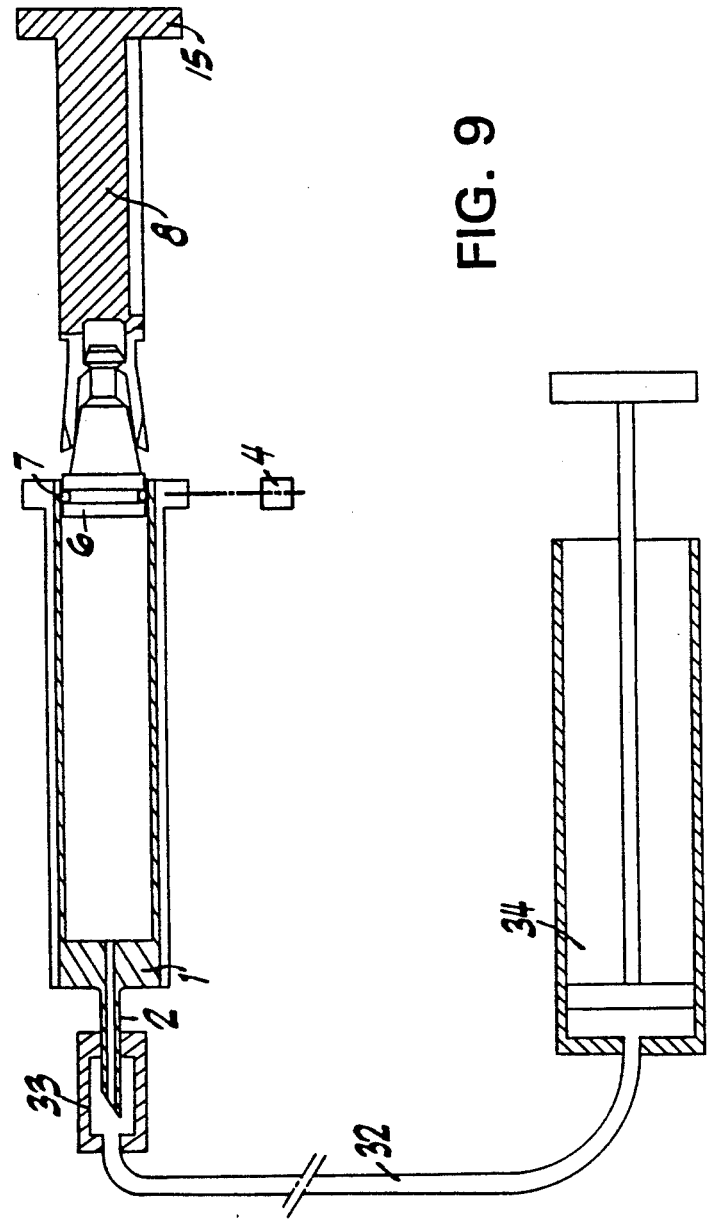

SINGLE USE DISPOSABLE SYRINGE

DESCRIPTION

1. Field of the Invention

The present invention relates to disposable syringes which are rendered non-reusable after a first injection therewith.

2. Background and Prior Art

Syringes disposable after a single use are being used more and more to avoid the risks of contamination from using a syringe poorly sterilized after a first use.

However, contaminations are due to the use by drug-addicts of previously used syringes which are not sterilized or poorly sterilized.

In order to avoid such accidents, syringes have been proposed which are rendered automatically non-usable after a first injection.

U.S. Pat. No. 3 934 586 (Easton et al) describes pre-filled syringes which make it possible to inject several successive doses.

The operating rod of these syringes bears stops which abut one another on the end of the barrel and which are broken along an oblique line of maximum weakness which leaves a sharp edge which scores the wall of the barrel. Such syringes cannot be re-used.

Patent De-A-1 965 761, FR-A-2 027 681, U.S. Pat. No. 3 667 657 (Chiquiar-Arias) describe pre-filled syringes which comprise a small knife which is fixed laterally on the operating rod and which is engaged in an opening in the cylindrical barrel. These syringes cannot be sold empty to be filled by the user as, as soon as the piston is driven into the barrel, the knife cuts the latter.

U.S. Pat. No. 3 951 146, DE-A-2 354 628, FR-A-2 204 429 (Chiquiar-Arias) describes syringes in which the operating rod bears a casing or a notch in which is housed a small knife which is pushed radially by a spring and which presents a rounded rear edge and a cutting front edge. It is possible to withdraw the piston rearwardly in order to suck liquid into the barrel without scratching the wall of the barrel. In order to drive the piston to the bottom of the barrel, a protection sheet is engaged between the wall of the cylindrical barrel and the cutting blade which is removed thereafter.

The problem to be solved is to provide self-destroying syringes which may be sold empty and which make it possible firstly to drive the piston in the barrel in order to drive out the air without scratching the barrel, then to withdraw the piston rearwardly in order to suck in a liquid without scratching or cutting the wall of the barrel, then to drive the piston again into the barrel in order to inject the dose of liquid contained therein, while cutting or scratching or breaking the wall of the barrel in order to render the syringe unusable a second time.

SUMMARY OF THE INVENTION

A syringe according to the invention comprises a cylindrical barrel, a piston displaceable inside said barrel, a rod for moving said piston and a cutting member which scratches or cuts or breaks the wall of said barrel during the injection of the liquid contained in said barrel.

The solution of the aforesaid problem consists in a syringe in which one end of the rod and said piston are connected by means which allow a relative axial displacement and either the rod or piston bears at least one flexible finger, which bears at its free end a cutting member, whilst the other bears a deviation means which cooperates with said flexible finger to deform the latter by pushing said cutting member outwardly when said end of the rod and said piston approach one another, with the result that, when the rod is withdrawn rearwardly in order to fill the syringe with the liquid to be injected, said flexible fingers occupy a position in which said cutting members are retracted inside said barrel and do not touch the wall thereof and when said piston is driven into said barrel, pushing on the rod to inject the liquid, said flexible fingers move apart and said cutting members are pushed outwardly and cut or scratch the wall of the barrel, which renders the syringe unusable a second time.

According to a first embodiment, said piston or one end of the rod bears one or more ramps inclined with respect to the axis of the syringe against which said flexible fingers slide, moving apart towards the outside when the rod and said piston approach each other axially and retracting towards the inside when the rod and said piston approach each other axially and retracting towards the inside when the rod and said piston move apart axially from each other.

According to another embodiment, each of the flexible fingers is connected to the piston or to one end of said rod by an articulated connected rod which pushes said flexible finger outwardly when said piston and said rod approach each other axially and which returns said flexible finger inwardly when said piston and said rod move apart axially from each other.

A process for manufacturing a non-reusable syringe according to the invention comprises the following operations:

connecting one end of the rod to said piston by connected means which allows a relative axial displacement of small amplitude and providing the rod or piston with at least one flexible finger which bears a cutting member while the other is provided with a deviation means which cooperates with said flexible finger in order to move the finger outwardly when said rod and said piston axially approach each other and to allow the finger to retract inwardly when said piston and said rod move axially away from each other;

placing between a flange of the barrel and a disc on the end of the rod a safety distance piece in order to avoid, in the event of accidental abutment on the rod during handling, packing or unpacking of the syringe, piercing of the wall of the barrel, which would prematurely render the syringe unusable;

connecting the end of said provided with the needle support or an incorporated needle to a suction means to drive said piston in said barrel without said cutting members cutting or scratching said barrel.

The invention results in novel disposable syringes which cannot be reused after a first injection.

The syringes according to the invention have the advantage of being able to be delivered, unfilled, with the piston driven in the barrel of the syringe, this operation being effected in the factory by connecting the syringes to a suction means which sucks the piston towards the bottom of the syringe so that the cutting members are retracted during this operation and do not risk scratching or cutting the wall of the barrel.

The syringes according to the invention also have the advantage that the cutting members are pushed radially by a force which is proportional to the axial thrust exerted on the rod during injection, so that the penetration of the cutting members in the wall of the barrel is better ensured than in the known syringes where the knife is pushed radially by a spring exerting a constant thrust.

The freedom of relative axial displacement of the rod with respect to the piston of the syringe makes it possible to obtain a spacing of the knives towards the outside when one presses on the rod but also a retraction of the knives towards the inside when the rod moves axially away from the piston, i.e. when one pulls on the rod to suck liquid or when the piston is sucked to drive it in the syringe, with the result that, during these two operations, the cutting members do not risk cutting or scratching the wall of the barrel.

BRIEF DESCRIPTION OF THE DRAWINGS

The following description refers to the accompanying drawings which show, without any limiting character, embodiments of syringes according to the invention.

FIG. 1 shows in axial section a disposable syringe according to a first embodiment.

FIG. 2 shows in partial axial section the same disposable syringe according to the invention during use.

FIG. 3 is a transverse section along line III—III of FIG. 2.

FIGS. 9 and 10 show steps for carrying out the process of manufacture according to the invention.

DETAILED DESCRIPTION

Figures 4, 5:
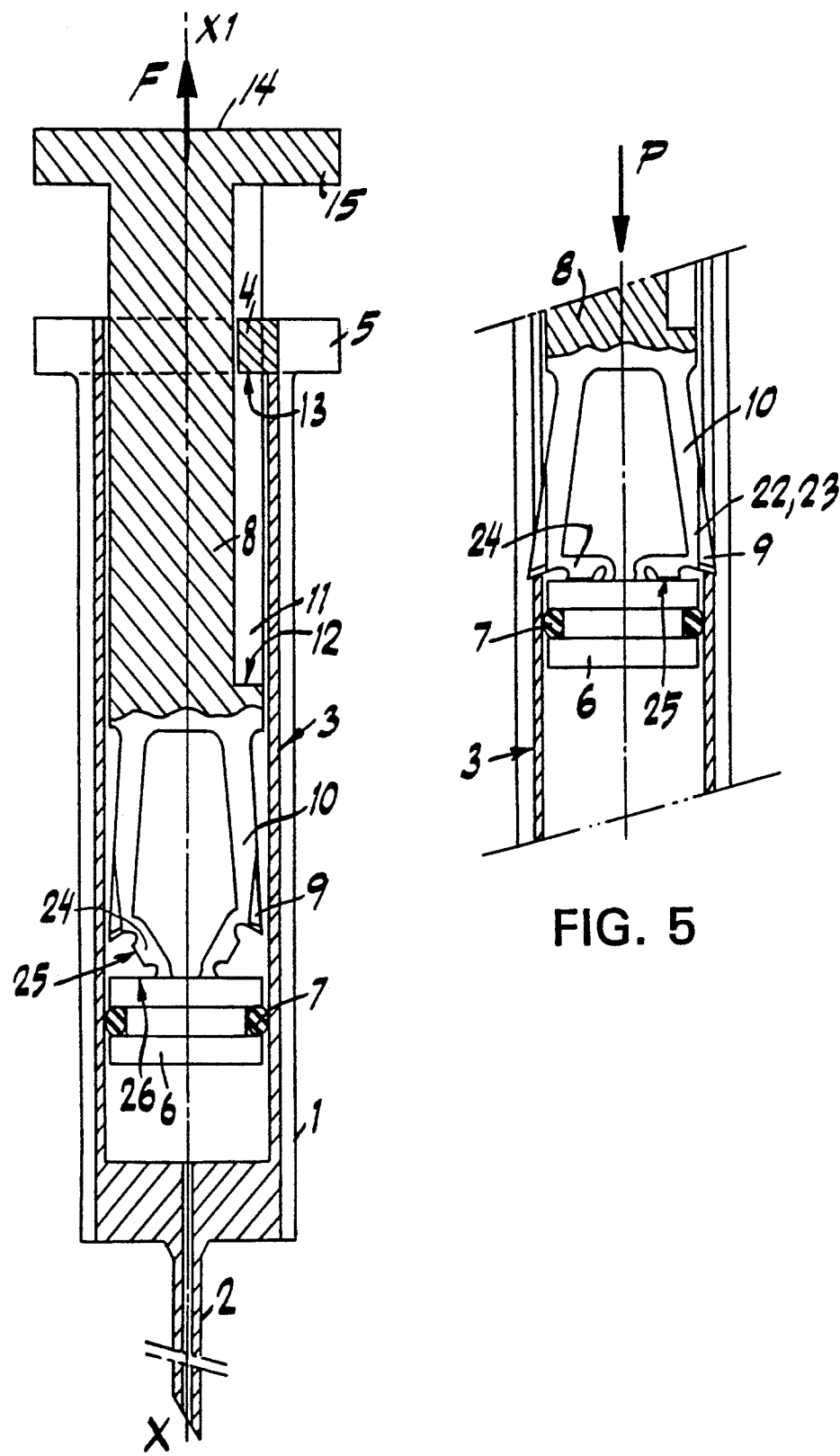
FIG. 4 shows in axial section a second embodiment of disposable syringes according to the invention.
FIG. 5 shows, in partial axial section, the same embodiment as in FIG. 4, under conditions of use identical to those of FIG. 2.

As indicated in FIGS. 1 to 3, a disposable syringe comprises a cylindrical barrel 1 with axis XXI which is provided at one end with a needle 2. An operating rod 8 and a piston 6 which slide in said barrel.

The rod 8 has a groove 11, extending longitudinally and parallel to the axis, XXI said groove being bounded at one end by a disc 15 and at the other end by a stop 12 connected to rod 8.

The barrel 1 advantageously comprises at one end a flange 5 on which is added, after positioning the rod 8 in said barrel, a guide bead 4 which penetrates in said groove.

The bead 4 extends into 11 and groove allows the rod 8 to slide with respect to said barrel but prevents rotation of said rod with respect to said barrel.

Said bead 4 has a face 13 which forms a stop, with the stop 12 connected to the rod, 8 with the result that, when an attempt is made to extract said rod from said barrel, the face 12 comes into contact with the stop 13 and therefore prevents the extraction.

This prevents the user from removing the cutting members to be described hereafter.

In a preferred embodiment, the wall of said barrel comprises at minimum one zone 3 of least resistance, for example a groove which extends along a generatrix of said cylindrical barrel substantially over the entire length of said barrel.

Said piston advantageously comprises sealing means 7.

The syringe according to the invention comprises at least one pointed and cutting projection of any other cutting or breaking means 9 such as a blade, sharp edge or knurl 30 adapted to produce grooving, permanent deformation, cutting perforation or breaking into fragments of said barrel, with the result that the latter can no longer cooperate with said piston so as to permit pumping of the fluid, and therefore it prevents subsequent use of the syringe for the purpose of injecting said fluid.

In the following specification, in order to facilitate reading thereof, said means will be designated by the generic term cutting member 9.

In the embodiments according to the invention, said cutting members are mounted at the free end of flexible fingers 10 which are themselves connected to an end of said rod 8 or said piston 6.

In the embodiment shown in FIG. 3, the syringe comprises two flexible fingers.

In the embodiments according to the invention shown in FIGS. 1, 2, 4, 5, 6, 7, 8, 9, said flexible fingers are connected to an end of rod.

In a first embodiment according to the invention, said piston comprises at least one deviation surface 16 which is constituted for example by a truncated surface as shown in FIGS. 1 and 2, or by an oblique ramp with respect to axis $XX_1$, against which the fingers come into contact.

In FIG. 1, said deviation surface cooperates with said flexible fingers which occupy a position in which the latter are retracted inside said barrel and do not touch the wall thereof.

In FIG. 2, said deviation surface cooperates with said flexible fingers in order to deform them by pushing said cutting members outwardly when said end of the rod and said piston approach each other, subsequent to the application of a thrust represented by arrow P on rod so that said cutting members cut or scratch the wall of said barrel, which renders the syringe unusable a second time.

Such changes in position of said flexible fingers are due on the one hand to the flexibility of the fingers and on the other hand to the relative approach or moving apart of said piston and said manoeuvring rod, these movement being said possible by the particular structure of the connecting means between and said piston.

In fact, in this embodiment, FIGS. 1 and 2 show that said piston comprises a rod 17 and a head 18 which terminates in a face 21, while the opposed end of rod 8 comprises a housing 31 limited by a bottom face 20, said flexible fingers comprising catches 19.

The flexibility of the fingers makes it possible, when assembling the syringe, for said head 18 on the piston to penetrate in housing 31 in the rod so that catches 19 engage behind head 18 whereby the rod and piston are connected with freedom of relative axial displacement.

FIG. 2 shows that such relative axial displacement is limited in the direction of approach between said rod and said piston, by the contact of said surface 21 and of said bottom face 20, with the result that the spacing apart of the flexible finger subsequent to such approach is thus limited.

Moreover, FIG. 3 shows that said flexible fingers comprise bearing faces 22 and 23 located in the immediate vicinity of the cutting members 9, said bearing faces cooperating with the inner wall of said barrel, thus limiting the spaced apart relationship of said cutting members, with the result that, during cutting, the cutting members do not project outside said barrel and cannot injure the user.

In FIGS. 4 and 5, analogous parts of FIGS. 1 and 2 are shown with the same references.

FIGS. 4 and 5 show another embodiment according to the invention in which said flexible fingers 10 are connected at one end to rod 8 and at the other end to said piston 6 via connecting rods 24 articulated at their two ends, the connecting means between rod 8 and piston 6 thus defined allowing the spacing apart and retraction of said cutting members corresponding respectively to the relative approach and spacing apart of said rod and said piston.

In fact, FIGS. 4 and 5 show that said connecting rods 24 comprise a substantially rigid central part which itself comprises a surface 25 which forms a stop, and two end of a section and rigidity substantially less than the central part with the result that said ends of the connected rod which are connected, one to said piston, the other to said flexible finger, may be deformed and thus constitute an articulation joint.

FIG. 4 shows that, after application of a traction force to rod represented by arrow F, the forces of traction are transmitted by said flexible fingers to said connecting rods and by said connecting rods to said piston.

Taking into account the resistance to sliding of said piston in said barrel due to the friction of the latter and said sealing means, the ends of said connecting rods performing the role of articulation joints on being deformed, said connecting rods move, provoking retraction inside the barrel of the cutting members simultaneously with the relative moving apart of said rod and of said piston.

FIG. 5 shows that after the application of a thrust on the rod, represented by arrow F, the force transmitted by said flexible fingers lead to a deformation of the ends of the connecting rods 24 to cause displacement of the cutting members 9 towards the wall of said barrel, with the result that, when the piston is driven into said barrel, said cutting members cut or scratch said inner wall of said barrel.

Figure 6:
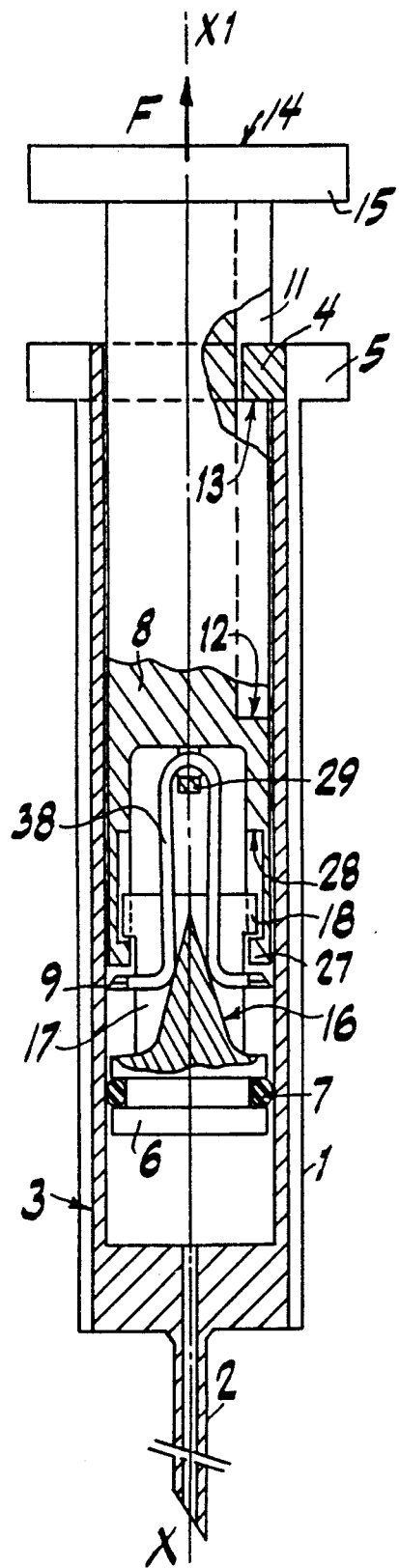
FIG. 6 shows in axial section a third embodiment of disposable syringes according to the invention.
Figure 7:
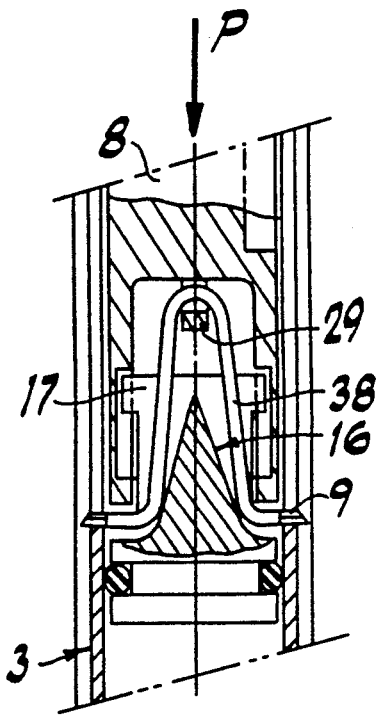
FIG. 7 shows in partial axial section the same disposable syringe in use.

FIGS. 6 and 7 show a third embodiment according to the invention. The analogous parts of FIGS. 1 and 2 are represented by the same references.

Piston 6 comprises a rod 17 and a head 18 slidable in a housing 31 arranged at the end of rod 8 which itself comprises catches 27 and a bearing face 28, which allows a relative axial displacement between the rod 8 and the piston 6.

Inside said piston rod 17 are two inclined surfaces 16 which form two oblique ramps which converge in the direction of the rod 8.

An elastic pin 38 in the form of a U constitutes a pair of flexible fingers whose ends are bent and bear cutting members 9.

Said pin is seemed to rod 8 by a connecting means 29 such as a clamp, ring or any other equivalent fixing means.

In FIG. 6, the surfaces 16 cooperate with said flexible fingers so that the latter retract inside said cylindrical barrel without touching the wall thereof, when said piston moves away from said rod.

FIG. 7 shows that, during injection of the liquid under the action of a thrust by the user on rod 8, represented by arrow P, said deviation surfaces excert forces outwardly, due to the approach of said piston and said rod, to cause said cutting members to cut said wall.

In the embodiment shown in FIGS. 6 and 7, the deviation surfaces, in the form of inclined ramps, may advantageously be constituted by the bottom of a groove made in said rod 17, the sides of said groove serving to guide the flexible fingers during the relative movements between said piston and said rod 8.

Figure 8:
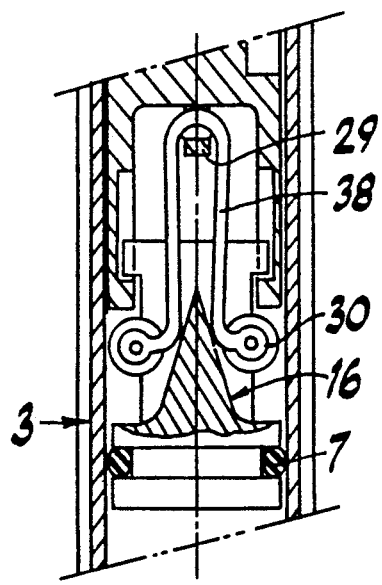
FIG. 8 shows in partial axial section a fourth embodiment of disposable syringes according to the invention.

FIG. 8 shows a variant according to the invention, in which the cutting members are constituted by knurls 30, particularly for when said barrel is made of a breakable material such as glass, plastics materials of polycarbonate type, which, under the pressure exerted by said knurls according to the same principles as developed for the other embodiments, will break into fragments or burst.

In this embodiment, the cylindrical barrel may be covered on the outside with a supple film which forms a jacket avoiding dispersion of the fragments resulting from the breakage. The breakage advantageously occurs in the zone of least resistance 3 constituted by a groove made in the barrel, said groove being filled with a supple resin which avoids the dispersion of the fragments resulting from the breakage.

FIG. 9 shows the process of manufacturing the disposable syringes according to the invention and more particularly the process which consists in guiding said piston in the bottom of said barrel without damaging the latter and enabling empty syringes ready to be filled by suction to be delivered.

At least one tube 32, is equipped with a connecting device 33 fixed on the end of the needle 2 of the syringe.

Tube 32 is connected at its other end to suction means 34 such as a pump, for example.

The four principal pieces of the syringe, viz. said barrel, said piston, said rod, said bead, may be manufactured separately.

In that case, said need an said piston is engaged in said housing provided in said rod.

In a variant, the rod and the piston are assembled together.

Said piston is then presented in said barrel so that the sealing means 7 are introduced as shown in FIG. 9, taking care to maintain said rod remote from said piston thanks to the structure of the connecting means described in the above paragraphs, with the result that said flexible fingers are in a retracted position and do not damage said barrel when they are made to penetrate therein.

When said suction means is actuated, said piston is subjected to a force due to the difference in pressure existing between its faces, which force produces its displacement towards the bottom of said barrel: the flexible fingers remain in their retracted position during this movement. The piston drives the rod in its movement. Finally, said bead 4 is mounted on said flange and there is placed between the flange 5 of the barrel and the disc 15 of the end of the rod 8 as shown in FIG. 10, a safety spacer device 39 in order to avoid, in the event of accidental pressure on the rod, 8 during handling, packing or unpacking of the syringe, cutting of the wall of the barrel before use, which would prematurely render the syringe unusable.

FIGS. 11 to 16 show three other embodiments of a syringe according to the invention in which said barrel comprises said zone of least resistance 3 which extends along a generatrix of said cylindrical barrel.

Figure 11:
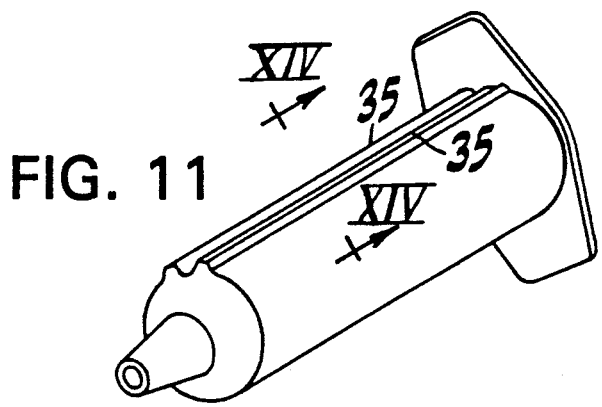
FIGS. 11, 12 and 13 show three particular embodiments of the cylindrical barrel of disposable syringes according to the invention.
Figure 14:
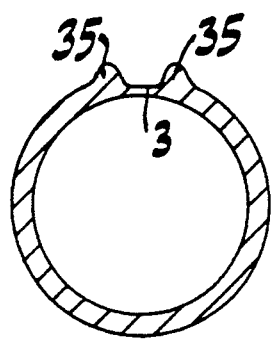
FIG. 14 is a section along XIV—XIV of FIG. 11.
Figure 15:
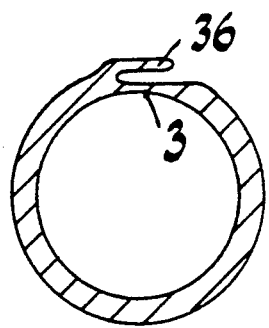
FIG. 15 is a section along XV—XV of FIG. 12.

In an embodiment shown in FIGS. 11 and 14, said wall of said barrel comprises two projecting zones 35 which extend along two generatrices of said barrel, on either side of said zone of least resistance 3, and form two beads so that, when said barrel is cut by said cutting members, said projecting zones prevent any accidental contact between said cutting members and the user.

Figure 12:
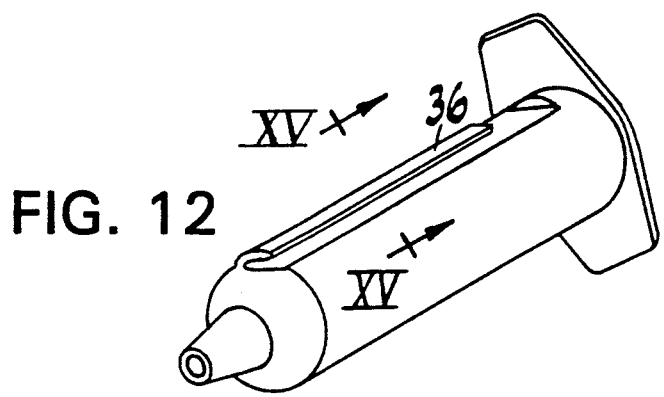
Figure 13:
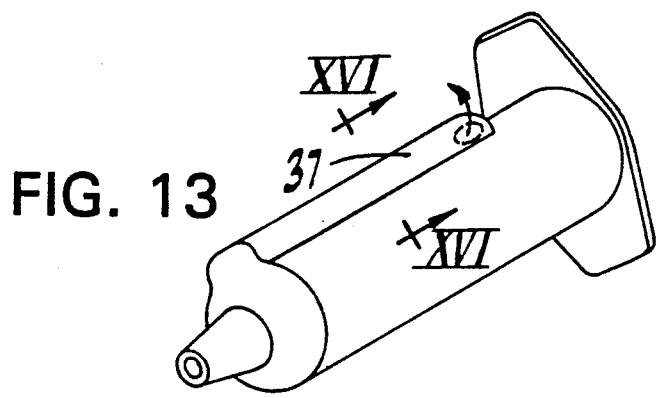

FIGS. 12 and 13 show another variant in which said wall comprises one single projecting zone, in the form of a tongue 36, which partially covers said zone of least resistance 3.

Figure 16:
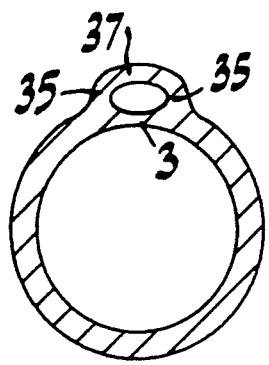
FIG. 16 is a section along XVI—XVI of FIG. 13.

FIGS. 13 and 16 show a variant according to the invention in which said projecting zones 35 located on either side of zone 3, join to form a tongue 37 which completely covers said zone 3.

The embodiments of a syringe according to the invention shown in FIGS. 11 to 16 make it possible to avoid andy risk of said cutting members injuring the user.

The relative arrangements of the fingers and the deviation surfaces with respect to the piston and to the rod may, of course, be reversed without the operation being modified.

I claim:

1. A singe use disposable syringe comprising:
a barrel having an axis,
a piston member axially slidable in said barrel in a retraction movement to fill the barrel with fluid and a forward movement to discharge fluid from the barrel,
an operating rod member projecting from said barrel for operating said piston member and being operatively connected to said piston member with capability of relative axial movement therebetween to approach said piston member during forward movement of said piston member,
a flexible finger having an end connected to one of said members,
cutting means on said flexible finger spaced from said one end thereof and facing said barrel, and
deviation means for displacing said flexible finger outwardly during approach of said operating rod member towards said piston member upon forward movement of said piston member to produce cutting of said barrel by said cutting means to render said barrel subsequently unusable, said flexible finger having a normal position, when not displaced by said deviation means, in which said cutting means is retracted from said barrel during retraction movement of said piston member.

2. A syringe as claimed in claim 1, wherein said deviation means comprises an oblique ramp having an inclined surface contacting said flexible finger to move said finger towards said barrel when said operating rod member and said piston member approach one another.

3. A syringe as claimed in claim 1, wherein said deviation means comprises a body have a conical surface contacting said flexible finger.

4. A syringe as claimed in claim 1, comprising a second flexible finger and corresponding cutting means on said one member in diametric opposition to the first said flexible finger.

5. A syringe as claimed in claim 1, wherein said deviation means comprises a conical surface slidably emerging said finger member.

6. A syringe as claimed in claim 1, comprising means coupling the rod member and the piston member for relative axial movement, comprising a piston rod on said piston member and a head on said piston rod, said rod member have a housing in which said head is slidable and catch means retaining said head in said housing.

7. A syringe as claimed in claim 1, wherein said deviation means comprises an articulated connecting rod joining said piston and rod members to permit limited relative axial movement thereof, said articulated connecting rod being connected to said flexible finger to produce outward displacement thereof when the piston and rod members approach one another.

8. A syringe as claimed in claim 1, wherein said barrel is constituted of a breakable material, said cutting means comprising a barrel member which breaks said barrel when displaced thereagainst.

9. A syringe as claimed in claim 1, comprising an elastic pin with flexible arms each constituting one said flexible finger.

10. A syringe as claimed in claim 1, wherein said barrel has a zone of minimum resistance facing said cutting means.

11. A syringe as claimed in claim 1, wherein said barrel is cylindrical and has a zone of minimum resistance facing said cutting means extending along a generatrix of said barrel.

12. A syringe as claimed in claim 11, comprising a tongue on said barrel covering at least a portion of said zone of minimum resistance.

13. A syringe as claimed in claim 1, comprising a bead on said barrel engaging said rod member to permit sliding movement of said rod member in said barrel while preventing relative rotation between said rod member and said barrel.

14. A syringe as claimed in claim 13, comprising flange means on said operating rod member cooperating with said bead for limiting the movement of said rod member in said barrel.

15. A syringe as claimed in claim 14, comprising removable stop means interposed between said operating rod means and said barrel to temporarily block relative movement therebetween.

16. A syringe as claimed in claim 1, comprising means for limiting outward movement of said flexible finger to prevent said cutting means from extending outwardly of said barrel.

* * * * *